United States Patent [19]

Dubois et al.

[11] Patent Number: 4,772,734
[45] Date of Patent: Sep. 20, 1988

[54] TANTALUM CATALYSTS FOR THE DIMERIZATION OF OLEFINS

[75] Inventors: Robert A. Dubois, Franklin; Richard R. Schrock, Winchester, both of Mass.

[73] Assignee: The Dow Chemical Company, Midland, Mich.

[21] Appl. No.: 74,657

[22] Filed: Jul. 17, 1987

Related U.S. Application Data

[62] Division of Ser. No. 26,358, Mar. 16, 1987, Pat. No. 4,717,783.

[51] Int. Cl.$^4$ .............................................. B01J 23/20
[52] U.S. Cl. ....................................... 556/11; 502/150; 502/152; 502/154; 502/158; 502/171; 502/246; 585/511
[58] Field of Search ............... 502/150, 152, 154, 158, 502/171, 246; 585/511; 556/11

[56] References Cited

U.S. PATENT DOCUMENTS 4,197,419  4/1980  Schrock .............................. 585/511
4,231,947 11/1980  Schrock .............................. 556/13
4,245,131  1/1981  Schrock .............................. 585/511

OTHER PUBLICATIONS

"Substituted Biscyclopentadienyl Tantale Complexes; Synthesis and Reactivity of Dichlorides, TRI-and Monohydrides", LeBlanc et al., C. R. Acad. SC. Paris, t. 295 (8 Nov. 1982), Serdes II pp. 795-797.

P. A. Belmonte et al., Journal of the American Chemical Soc., 105, 2643-2650 (1983).

S. Muthukumaru Pillai et al., Chemical Reviews, 86, 353-399 (1986).

B. Bogdanovic, Advances in Organometallic Chemistry, 17, 105-140, (1979).

S. J. McLain et al., Journal of the American Chemical Society, 101, 4558-4570 (1979).

S. J. McLain et al., Journal of the American Chemical Society, 102, 5610-5618 (1980).

Primary Examiner—Patrick P. Garvin
Assistant Examiner—George R. Fourson
Attorney, Agent, or Firm—Marie F. Zuckerman

[57] ABSTRACT

1-Butenes are selectively produced via the dimerization of 1-olefins in the presence of novel organotantalum catalysts comprising tantalum and a silyl-substituted cyclopentadienyl moiety having the formula $C_5H_{5-x}(SiR^6_3)_x$, wherein each $R^6$ may be the same or different and is hydrogen, alkyl, cycloalkyl, aryl, aralkyl or alkoxy, and x is an integer from 1 to 5.

13 Claims, No Drawings

TANTALUM CATALYSTS FOR THE DIMERIZATION OF OLEFINS

CROSS-REFERENCE TO RELATED APPLICATION

This is a divisional of application Ser. No. 026,358, filed Mar. 16, 1987, now U.S. Pat. No. 4,717,783.

BACKGROUND OF THE INVENTION

This invention relates to tantalum compounds which are catalysts or catalyst precursors for the dimerization of 1-olefins to 1-butenes.

Higher olefins, such as 1-butenes, find application as industrial intermediates. 2,3-Dimethyl-1-butenes, for example, are used as a gasoline additive to improve octane rating and as a starting material to synthesize musk perfumes.

The product of the dimerization of a terminal olefin is dependent on the direction of coupling of the two olefinic units; hence, a mixture of dimeric products is always possible. In order to achieve a high yield of a particular dimeric product, a highly selective catalyst is required. Prior to 1980 few homogeneous catalysts were known for converting a terminal olefin selectively to 1-butene or 2,3-disubstituted-1-butenes at room temperature or above. In addition, the known catalysts readily isomerized the initially formed 1-butenes to the thermodynamically more stable internal olefins. Moreover, some of the catalysts were active with only one olefinic substrate. Certain nickel compounds containing phosphine ligands typify the dimerization catalysts of this period. One example of said nickel compounds is tris(triisopropylphosphine)nickel(O), which in the dimerization of propylene, yields a mixture of dimethylbutenes, methylpentenes and linear hexenes. For a general review of this subject, see B. Bogdanovic, *Advances in Organometallic Chemistry*, 17 (1979), 105-140; and S. Muthukumari Pillai et al., *Chemical Reviews*, 86 (1986), 353-399.

More recently a series of tantalum compounds has been disclosed in U.S. Pat. Nos. 4,197,419; 4,231,947; and 4,245,131. It is further disclosed that these tantalum compounds are capable of selectively dimerizing 1-olefins, in general, to 1-butene and 2,3-disubstituted-1-butenes. These tantalum compounds contain a cyclopentadienyl group represented by the formula $C_5H_{5-x}Me_x$, wherein Me is methyl and x is an integer from 0 to 5. The tantalum compounds containing this cyclopentadienyl group and their use as catalysts in the dimerization of 1-olefins are described hereinbelow.

U.S. Pat. No. 4,197,419 discloses tantalum catalyst precursors or catalysts of the formulae $$Ta(C_5Me_5)(X)_2L$$

and

where $C_5Me_5$ is pentamethylcyclopentadienyl; X is halide or alkoxide; L is an alkene having from 2 to 20 carbon atoms; and $R^2$ is hydrogen or a $C_{1-18}$ alkyl radical. These precursors or catalysts are disclosed to dimerize 1-olefins, such as 1-propylene, 1-pentene and 1-hexene, to 1-butenes selectively. For example, it is taught that propylene is dimerized with greater than 90 percent selectivity to 2,3-dimethyl-1-butene at a rate of about 0.039 min$^{-1}$ or about 1 turnover per Ta per hour at 40° C.

U.S. Pat. Nos. 4,231,947 and 4,245,131 disclose catalysts or catalyst precursors of the formula $Z(R)(R^1)_n(R^2)(A)_m$ wherein Z is tantalum or niobium: R is cyclopentadienyl or methyl-substituted cyclopentadienyl having the formula $C_5H_xMe_{5-x}$, wherein x is an integer from 0 to 5, or R is neopentylidene; $R^1$ is benzyl or neopentyl, n is 0 or 1; $R^2$ is neopentylidene, benzylidene, tetramethylene or 2,3-dimethyltetramethylene; A is halo including chloro, bromo, iodo and fluoro or a moiety of the formula $YR^3R^4R^5$ wherein Y is a group element including N, P, Sb and Bi, and $R^3$, $R^4$ and $R^5$ can be the same or different and $C_{1-4}$ alkyl, aralkyl or aryl; and m is 1 or 2. In the dimerization of propylene by tgTa($C_5H_5$)(CHCMe$_3$)(Cl)$_2$], it is taught that 2,3-dimethyl-1-butene is produced in 93 percent selectivity at a rate of 2 moles per Ta per hour at 45° C.

The preparation of the methyl-substituted cyclopentadienyl group of the aforementioned catalysts is lengthy and costly: for example, the synthesis of lithium pentamethylcyclopentadienide is described in four steps in Scheme 1. Commercially unavailable 2-bromo-2-butene is reacted with lithium, and the lithiated product is condensed with ethyl acetate. The condensation product is cyclized and the resulting pentamethylcyclopentadiene ring compound is reacted with butyl lithium. These reactions give lithium pentamethylcyclopentadienide, the anion of which can be introduced into a tantalum compound.

SCHEME 1

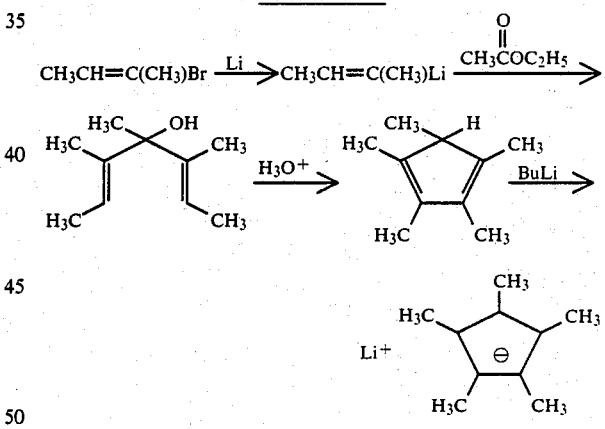

One skilled in the art can readily appreciate the difficulties and cost of preparing lithium pentamethylcyclopentadienide by the reactions outlined in Scheme 1. Moreover, after the substituted cyclopentadienide group is prepared, the synthesis of the tantalum catalysts containing said cyclopentadienyl group must be accomplished. The prior art patents cited hereinabove teach the synthesis of such catalysts; but, again the synthesis is lengthy and costly.

In view of the prior art it would be desirable to provide a catalyst system which could be prepared easily from commercially available starting materials and which could find use in the selective dimerization of 1-olefins to 1-butenes. Additionally, it would be desirable if the easily prepared catalyst would possess a higher activity in the dimerization of 1-olefins than the homogeneous catalysts known heretofore.

SUMMARY OF THE INVENTION

In one aspect, this invention is novel organotantalum compounds which comprise tantalum and a cyclopentadienyl group containing at least one tri-substituted silyl moiety. The silyl-containing cyclopentadienyl group of this invention can be easily prepared from commercially available starting materials. Consequently, this invention provides organotantalum compounds which require less effort to synthesize than the organotantalum compounds of the above-cited prior art patents.

In another aspect, this invention is a process for the selective dimerization of a 1-olefin to a dimer having a 1-butene moiety which is optionally substituted at the 2,3-carbon atoms, said process employing the novel organotantalum compounds as catalysts. The process of this invention comprises contacting a 1-olefin with an organotantalum catalyst under reaction conditions such that a dimer having a 1-butene moiety which is optionally substituted at the 2,3-carbon atoms is formed; said catalyst comprising tantalum and a cyclopentadienyl group containing at least one tri-substituted silyl moiety. The tantalum catalysts of this invention can be advantageously used in the dimerization of any one of a plurality of unsubstituted or substituted 1-olefin feed compositions. Surprisingly, the tantalum catalysts of this invention exhibit a higher activity towards the dimerization of 1-olefins than the tantalum dimerization catalysts known heretofore.

DETAILED DESCRIPTION OF THE INVENTION

The novel compounds of this invention are organotantalum compounds comprising tantalum and a cyclopentadienyl group containing at least one tri-substituted silyl moiety. Preferred novel compounds of this invention are represented by one of the formulae:

(I)

wherein X is a halide, including chloride, bromide, iodide and fluoride, or an alkoxide; L is an alkene having from 2 to 20 carbon atoms and which can be substituted with alkyl or aryl, and $Cp^{s,x}$ is a substituted cyclopentadienyl group, defined hereinafter;

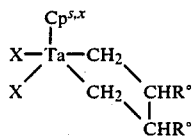
(II)

wherein X is defined in (I) above, $R^o$ is hydrogen or a $C_{1-18}$ alkyl, such as ethyl, propyl or butyl, and $Cp^{s,x}$ is defined hereinafter; and

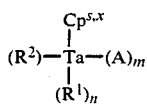
(III)

wherein $R^1$ is benzyl or neopentyl; n is 0 or 1; $R^2$ is neopentylidene or benzylidene; A is halide or a moiety of the formula $YR^3R^4R^5$ wherein Y is a Group Va element, including N, P, Sb and Bi, and $R^3$, $R^4$ and $R^5$ can be the same or different and are $C_{1-4}$ alkyl, aralkyl such as benzyl, neopentyl, toluyl or xylyl, aryl such as phenyl, naphthyl or bipyridyl; m is 1 or 2; and $Cp^{s,x}$ is defined hereinafter.

$Cp^{s,x}$ represents cyclopentadienyl having at least one tri-substituted silyl moiety, such that $Cp^{s,x}$ has the formula $C_5H_{5-x}(SiR^6{}_3)_x$, wherein each $R^6$ is the same or different and is hydrogen; $C_{1-20}$ alkyl, such as methyl, ethyl, isopropyl; cycloalkyl, such as cyclohexyl; aryl, such as phenyl or toluyl; aralkyl, such as benzyl; or alkoxy, such as methoxy or ethoxy; and x is an integer from 1 to 5.

The novel tantalum catalysts, described hereinbefore, may be prepared in a two-part synthesis. The first part consists in synthesizing the $Cp^{s,x}$ group; the second part consists in synthesizing the novel tantalum compounds containing the $Cp^{s,x}$ group.

The $Cp^{s,x}$ compounds are easily prepared from commercially available cyclopentadiene metal salts, $M(C_5H_5)$. Lithium cyclopentadienide or sodium cyclopentadienide is a suitable starting material. The metal salt is reacted with a halo tri-substituted silane having the formula $R^6{}_3SiX$, wherein $R^6$ and X are defined hereinbefore, to yield cyclopentadiene containing at least one tri-substituted silyl moiety. Preferably, $R^6$ is a $C_{1-20}$ alkyl, aryl, or aralkyl moiety. More preferably, $R^6$ is a $C_{1-4}$ alkyl moiety. Most preferably, $R^6$ is a methyl moiety. Preferably, X is chloro. Examples of some commercially available halo tri-substituted silanes which may be used in the synthesis of $Cp^{s,x}$ are chlorotrimethylsilane, chlorotriethylsilane, chlorotriisopropylsilane, chlorotributylsilane, chlorotribenzylsilane, chlorotriphenylsilane, bromotrimethylsilane, bromotriethylsilane, iodotrimethylsilane, chlorosilane, bromosilane, chlorotrimethoxysilane and bromotriethoxysilane. The most preferred $R^6{}_3SiX$ is chlorotrimethylsilane.

The reaction of the cyclopentadienide metal salt with the halo tri-substituted silane is conducted under conditions such that cyclopentadiene containing at least one tri-substituted silyl moiety is obtained. Typically, the reaction temperature may be in the range 0° C. to 40° C., while the pressure is autogenous.

The tri-substituted silyl cyclopentadiene product has the formula $tgC_5H_{5-x}(SiR^6{}_3)_x]$, wherein $R^6$ and x are defined hereinabove. The degree of substitution on the cyclopentadiene ring will depend on the mole ratio of halo tri-substituted silane to unsubstituted cyclopentadienide. Thus, if said ratio is one, the cyclopentadiene product will be mono substituted (x=1). If said ratio is two, the cyclopentadiene product will be disubstituted (x=2); and so on. In those instances where x is 2 or greater, the substitution of each silyl moiety onto the cyclopentadienide ring is preferably carried out sequentially. For example, in order to prepare bis(tri-substituted silyl)cyclopentadiene, the mono derivative is converted to the corresponding cyclopentadienide metal salt by reaction, for example, with butyl lithium. The metal salt is reacted with a second mole of halo tri-substituted silane to obtain the desired bis(tri-substituted silyl)cyclopentadiene in which x=2. The preferred cyclopentadiene product contains two tri-substituted silyl moieties (x=2). The more preferred cyclopentadiene product contains two trimethylsilyl moieties and has the formula $1,3-tgC_5H_4(SiMe_3)_2]$.

In order to prepare the tantalum catalysts containing the silyl-substituted cyclopentadiene compound, said compound must be converted into the corresponding metal cyclopentadienide salt. It is from the salt form that the cyclopentadiene compound is transferred to a tantalum compound. Thus, in the final step, the cyclopentadiene compound containing the tri-substituted silyl moieties is reacted with butyl lithium to give LiCp$^{s,x}$ which has the formula Li[C$_5$H$_{5-x}$(SiR$^6_3$)$_x$], the Cp$^{s,x}$ of which can be incorporated into a tantalum compound.

The novel tantalum catalysts of this invention can be prepared by methods which are similar to those previously disclosed in U.S. Pat. Nos. 4,231,947 and 4,197,419. For example, compounds of Formula I are prepared by reacting TaX$_5$ with Zn(CH$_2$SiMe$_3$)$_2$, wherein X and Me are halide and methyl, respectively, at a temperature of between about 20° C. and 40° C. in toluene or pentane to give Ta(CH$_2$SiMe$_3$)X$_4$. The latter is reacted with LiCp$^{s,x}$ at a temperature of between 20° C. and 40° C. in toluene or diethyl ether to give TaCp$^{s,x}$(CH$_2$SiMe$_3$)X$_3$. Said TaCp$^{s,x}$(CH$_2$SiMe$_3$)X$_3$ is reacted with one-half mole of Zn(CH$_2$CH$_2$CH$_3$)$_2$ to give a compound of Formula I where L is propylene. Any other olefin, L, may be substituted for propylene by merely exposing TaCp$^{s,x}$(CH$_2$CHCH$_3$)X$_2$ to the desired olefin overnight at 25° C. Compounds of Formula II are prepared by equilibrating a compound of Formula I with an excess of olefin L.

The preparation of Formula III compounds will vary depending on the ligands involved. TaCp$^{s,x}$(CHCMe$_3$)Cl$_2$, for example, can be prepared by reacting TaCl$_5$ with Zn(CH$_2$CMe$_3$)$_2$ at a temperature between about 20° C. and 40° C. in toluene or pentane to form Ta(CH$_2$CMe$_3$)$_2$Cl$_3$. The latter compound is then reacted with LiCp$^{s,x}$ at a temperature of between about 20° C. and 40° C. in toluene or diethyl ether to form the desired product TaCp$^{s,x}$(CHCMe$_3$)Cl$_2$. Other representative compounds of Formula III encompassed by this invention include;

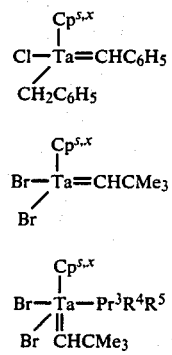

As described hereinbefore, the novel tantalum compound may contain a Group V donor having the formula YR$^3$R$^4$R$^5$. Examples of Group V donors which are suitable groups to incorporate into the novel tantalum compounds are the following: PMe$_3$, PMe$_2$Ph, PPH$_3$, NMe$_3$, NEt$_3$, AsMe$_3$, BiMe$_3$, P(OMe)$_3$, P(OPh)$_3$ wherein Me is methyl, Et is ethyl and Ph is phenyl. Optically active phosphines of the formula PR$^3$R$^4$R$^5$ are also suitable.

The novel tantalum catalysts of this invention are homogeneous in that they are in the same phase as the reactants under the conditions employed in the process. It is within the scope of this invention, however, for the tantalum catalysts to be used in a heterogeneous form by binding or physically adsorbing said catalyst onto a solid support. Such supports can be any material, providing it does not interfere with the dimerization reaction. Refractory oxides provide suitable supports. Such refractory oxides include alumina, silica, zirconia, boria, magnesia, titania, tantala, kieselgühr and mixtures of these materials. The support material can also be an activated carbon or a polymer, such as polystyrene. The support may be characterized by any pore size or pore shape, and may have any surface area, providing the support does not inhibit the activity of the tantalum catalyst. A description of suitable supports and their distinguishing features may be found in *Heterogeneous Catalysis in Practice* by C. N. Satterfield, (1980) at pages 86-94; and in "Polymer Supported Catalysts" by C. U. Pittman, Jr. in *Comprehensive Organometallic Chemistry*, G. Wilkinson, F. G. A. Stone, and E. W. Abel, eds., (1982), Volume VIII, at pages 553-611; and is incorporated herein by reference.

The supports disclosed hereinbefore may be chemically reacted with a tantalum catalyst precursor to give the tantalum catalyst chemically bonded to the support. Alternatively, the support may be treated with the tantalum catalyst or catalyst precursor, so as to obtain a tantalum catalyst physically adsorbed onto the support. The preparation of said supported catalysts is carried out by methods well-known in the art, for example, incipient wetness impregnation techniques and precipitation techniques, as described in detail in *Heterogeneous Catalysis in Practice*, by C. N. Satterfield, (1980) at pages 70-86.

In the practice of the method of the present invention, any one of a plurality of unsubstituted or substituted 1-olefin feed compositions may be employed in the dimerization reaction. In this context, the unsubstituted 1-olefin is defined as an acyclic aliphatic hydrocarbon having one double bond at the alpha, or first, carbon. The 1-olefin may be substituted with certain moieties, providing these moieties do not occupy a position on the doubly-bonded carbon atoms, namely the $\alpha,\beta$ or 1,2 carbons. It is desirable for these moieties to occupy a position at the third carbon or any carbon further along the chain. Those moieties which are suitable substituents will not interfere with the dimerization reaction. Such moieties include C$_{1-20}$ alkyl, such as methyl, ethyl or isopropyl: cycloalkyl, such as cyclohexyl: aryl, such as phenyl; aralkyl, such as benzyl: alkoxy, such as methoxy or ethoxy: and halo, such as chloro, bromo or iodo groups. It is desirable for the alkoxy and halo moieties to be located beyond the 4-carbon position along the chain. Examples of 1-olefins suitable for use in the dimerization reaction include the following: ethylene, propylene, 1-butene, 1-pentene, 1-hexene, 1-heptene, 1-octene, 1-nonene, 1-decene, 1-dodecene, 3-methyl-1-butene, 3-methyl-1-pentene, 4-methyl-1-pentene, 3-methyl-1-hexene, 4,4-dimethyl-1-pentene and 3,3-dimethyl-1-butene. Preferably, the 1-olefin is a C$_{1-12}$ 1-olefin. More preferably, the 1-olefin is a C$_{1-8}$ 1-olefin. Most preferably, the 1-olefin is propylene.

The tantalum catalyst is added to the 1-olefin in an amount which is sufficient to catalyze the dimerization reaction. Preferably, the weight percent of tantalum catalyst relative to 1-olefin substrate is in the range from about 0.01 weight percent to about 50 weight percent. Below the preferred lower limit, recovery of the catalyst becomes difficult and the efficiency of the reaction is too low. Above the preferred upper limit, the capacity of the reactor may be reduced, the product may be difficult to purify, and the economics may be disadvantageous. More preferably, the weight percent of the tantalum catalyst relative to 1-olefin is in the range from about 0.1 to about 5 weight percent.

The dimerization reaction may be carried out neat, if the 1-olefin substrate is a liquid under the process conditions or in a solvent, as desired. The solvent can be any compound which solubilizes the 1-olefin substrate, the dimerization products and the catalyst, and which is inert under the process conditions. Typical solvents include alkanes, such as pentane or hexane; aromatic compounds, such as benzene or toluene; chlorinated aliphatic or aromatic compounds, such as methylene dichloride or chlorobenzene. The weight ratio of solvent relative to 1-olefin substrate may vary from 0:1 to about 100:1: however, preferably the weight ratio is 0:1 to about 10:1.

Process conditions may vary over a wide range. Any reaction temperature and pressure may be maintained providing the 1-olefin feedstock is converted to the desired 1-butene or 2,3-disubstituted-1-butene dimerization product. The reaction temperature preferably ranges from about $-30°$ C. to about 200° C. Below $-30°$ C., the reaction is slow and the reaction time is inordinately long. Above 200° C., the product selectivity is reduced. The upper preferred limit may also be restricted by the boiling points of the reactants, solvents and products, and by the equipment at hand. More preferably, the reaction temperature ranges from about 25° C. to about 125° C. The reaction pressure preferably ranges from about 0.019 psig (1 mm Hg) to about 1000 psig. The preferred limits of pressure depend primarily on convenience and cost. Outside the stated limits costs increase and ease of operation decreases. More preferably, the reaction pressure ranges from about 14 psig to about 200 psig.

In accordance with the present invention, the dimerization of a 1-olefin to a dimer having a 1-butene moiety which is optionally substituted at the 2,3-carbon atoms may be conducted in any conventional reactor designed to withstand the pressure of the reaction. Thus, at pressures greater than atmospheric standard pressure, reactors, such as pressure bottles or metal autoclaves, may be employed. The reactor may be equipped with a means for controlling temperature, a means for measuring temperature and a means for agitating the reaction mixture.

For the purposes of the dimerization process of the present invention, the term "selectivity" refers to the mole percentage of the converted 1olefin which goes to a particular dimeric product. A dimer having a 1-butene moiety which is optionally substituted at the 2,3-carbon atoms is the major dimeric product of the process. Typically, a selectivity of at least about 70 mole percent is achieved in the production of said dimer. Preferably, the selectivity to a dimer having a 1-butene moiety which may be substituted at the 2,3-carbon atoms is at least about 80 mole percent; more preferably, the selectivity is at least about 90 mole percent; most preferably, the selectivity is at least about 95 mole percent.

For the purposes of the dimerization process of the present invention, the term "catalyst activity" refers to the rate at which the catalyst converts the 1-olefin to dimeric products. This rate is measured in units of moles of 1-olefin consumed per molar concentration of tantalum catalyst per hour, (mol. $M^{-1}$ hr.$^{-1}$). The catalyst activity is dependent upon the temperature of the reaction and the specific 1-olefin employed. Typically, the catalyst activity is at least about 1.36 mol. $M^{-1}$ hr.$^{-1}$ at 75° C., and at least about 4 mol. $M^{-1}$ hr.$^{-1}$ at 100° C. Preferably, the catalyst activity is at least about 1.36 mol. 1-octene $M^{-1}$ hr.$^{-1}$ at 75° C.; 4.0 mol. 1-octene $M^{-1}$ hr.$^{-1}$ at 100° C.; 2.0 mol. propylene $M^{-1}$ hr.$^{-1}$ at 75° C.; and 12.3 mol. propylene $M^{-1}$ hr.$^{-1}$ at 98° C.

ILLUSTRATIVE EMBODIMENTS

The following examples and comparative experiments will serve to illustrate the invention, but are not meant to limit the scope therein.

EXAMPLE 1

Preparation of TaCp$^{s,2}$Cl$_2$ (cyclooctene)

A. Preparation of Li{C$_5$H$_3$(SiMe$_3$)$_2$}

Trimethylsilylcyclopentadiene and bis(trimethylsilyl)cyclopentadiene are prepared by the procedures of Kraihanzel et al., *J. Amer. Chem. Soc.*, 90, 4701 (1968) and I. M. Pribytkova et al., *J. of Organometallic Chem.*, 30, C57-C60 (1971). Sodium cyclopentadienide (44 g, 0.50 mole) is added to 150 ml of tetrahydrofuran. Chlorotrimethylsilane (54 g, 0.5 mole) is added dropwise slowly to the reaction and the stirring is continued for 3 hours. The reaction mixture is poured into 150 ml of cold, distilled water and trimethylsilylcyclopentadiene is extracted into diethyl ether. The extract is rotary evaporated to remove the ethereal solvent and the residue is vacuum distilled to give trimethylsilylcyclopentadiene, b.p. 41° C.–43° C. (16 mm).

Freshly distilled trimethylsilylcyclopentadiene (1.6 g, 11.5 mmole) is dissolved in 10 ml of absolute ligroin. To this solution is added a solution of butyllithium (1.9N, 6.35 ml, 12.0 mmole) in ligroin dropwise with stirring. The mixture is stirred for one hour at room temperature. Chlorotrimethylsilane (2.6 g, 24 mmole) is added to the mixture under an argon sweep, and the resulting mixture heated for 3 hours at 40° C. The ligroin solution is filtered, the solvent evaporated, and the residue distilled under a vacuum to give 1,3-bis(trimethylsilyl)cyclopentadiene, b.p. 45° C./3 mm Hg.

1,3-Bis(trimethylsilyl)cyclopentadiene (10.5 g, 0.05 mole) is reacted with 32 ml of a 1.6M solution of butyllithium (0.05 mole) in hexane to give 6.3 g of lithium 1,3-bis(trimethylsilyl)cyclopentadienide.

B. Preparation of Catalyst

TaCp$^{s,2}$(CH$_2$SiMe$_3$)Cl$_3$ is prepared by the method of P. A. Belmonte et al., *J. Amer. Chem. Soc.*, 105, 2643 (1983). TaCp$^{s,2}$(CH$_2$SiMe$_3$)Cl$_3$ (500 mg, 0.856 mmole) is dissolved in 30 ml of toluene. The solution is cooled to $-30°$ C. under an atmosphere of argon. Zn(CH$_2$CH$_2$CH$_3$)$_2$ (71.3 mg, 0.47 mmole) is added with stirring. The orange-colored solution darkens and a small amount of precipitate forms. The reaction mixture is placed in a refrigerator at $-30°$ C. for 30 minutes, after which it is removed to an inert atmosphere and allowed to warm to room temperature with stirring. When the color of the solution is changed to deep purple, after approximately 2 hours, the solution is filtered. Cyclooctene (1 g, 0.91 mmole) is added to the filtrate and the reaction mixture is allowed to stand overnight at 25° C. The solvent is evaporated under reduced pressure (20 mm Hg) and the purple-black solid is recrystallized from pentane. {Ta[C$_5$H$_3$(SiMe$_3$)$_2$](Cl)$_2$(cyclooctene)} (420 mg, 86 percent yield) is obtained as black crystals.

The 90 MHz 1H nuclear magnetic resonance spectrum of {Ta[C$_5$H$_3$(SiMe$_3$)$_2$](Cl)$_2$(cyclooctene)} in benzene-d$_6$ shows the cyclopentadiene ring protons at $\tau$4.44 to 4.14 (split triplet, 3), the cyclooctene protons at $\tau$8.57 (broad singlet), and the protons of the trimethyl silyl groups at $\tau$9.90 (singlet, 18).

EXAMPLES 2(a)-(c)

Dimerization of 1-Octene

All liquid reagents are first deoxygenated in three freeze-pump-thaw cycles, then dried over molecular sieves, and dried again by passing through a column of activated alumina. 1-Octene is additionally treated to prevent catalyst deactivation. The additional pretreatment involves washing the 1-octene with aqueous ferrous sulfate twice; then drying the washed 1-octene over MgSO$_4$; deoxygenating the dried 1-octene in three freeze-pump-thaw cycles; and finally drying the deoxygenated 1-octene over molecular sieves under an inert gas atmosphere.

Example 2(a) is carried out as follows: TaCp$^{s,2}$Cl$_2$(cyclooctene) (150 mg, 0.263 mmole) is dissolved in 2.7 ml. of toluene in a 30-ml. screw cap vial in a drybox under an atmosphere of argon. Decane (150 $\mu$l, 109.5 mg, 0.77 mmole) is added to the solution for use as an internal gas phase chromatography standard. 1-Octene (1.57 g, 14 mmoles) is added to the solution. The reaction mixture is brought to the desired temperature by means of an oil bath. Aliquots are periodically removed from the reactor for analysis by capillary gas phase chromatography on a 25-meter, 5 percent phenylmethylsilicone column (flow rate of 1 ml/min He at 100/1 split injection, temperature programmed at 60° C. for 4 minutes rising to 180° C. at 16° C./minute).

Examples 2(b) and 2(c) are carried out in a manner analogous to Example 2(a). The results of Examples 2(a)-(c) are presented in Table I.

The predominant product is identified to be 2-hexyl-3-methyl-1-nonene, which is designated the tail-to-tail (tt) dimer. The secondary product is identified to be 2-hexyl-1-decene, which is designated the head-to-tail (ht) isomer. Other isomers, including internal olefinic dimers, are present in low yield.

TABLE I

| Ex. 2 | 1-Octene (g) | Catalyst Solvent (mg/ml) | T (°C.) | Selectivity* (mole %) | | |
|---|---|---|---|---|---|---|
| | | | | tt | ht | others |
| (a) | 1.57 | 150/2.7 | 50 | 83.7 | 15.9 | 2.4 |
| (b) | 3.14 | 109/5.4 | 75 | 77.0 | 16.9 | 6.1 |
| (c) | 3.14 | 16/5.4 | 100 | 78.3 | 20.5 | 6.0 |

*tt is the tail-to-tail dimer, 2-hexyl-3-methyl-1-nonene
ht is the head-to-tail dimer, 2-hexyl-1-decene others, include internal olefinic dimers The tail-to-tail dimer is obtained in a selectivity of greater than 70 percent under mild process conditions. At 50° C. the rate is found to be 0.08 mol. M$^{-1}$ hr.$^{-1}$. At 75° C. the rate is found to be 1.36 mol. M$^{-1}$ hr.$^{-1}$, and at 100° C. the rate is found to be 3.96 mol. M$^{-1}$ hr.$^{-1}$.

COMPARATIVE EXPERIMENT 1

A. Preparation of Ta(C$_5$Me$_5$)Cl$_2$(cyclooctene)

All operations are conducted under an atmosphere of argon. Ta(C$_5$Me$_5$)(CH$_2$CMe$_3$)Cl$_3$ (422 mg, 0.856 mmole), wherein C$_5$Me$_5$ is pentamethylcyclopentadienyl, and CH$_2$CMe$_3$ is neopentyl, is dissolved in 20 ml of toluene. The solution is cooled to −78° C. and Zn(CH$_2$CH$_2$CH$_3$)$_2$ (71 mg, 0.47 mmole) dissolved in 5 ml of toluene is added all at once. The reaction mixture is stirred for 15 minutes and then warmed to room temperature. A precipitate of ZnCl$_2$ is filtered off and 300 mg of cyclooctene is added. The reaction mixture is left to stand overnight at 25° C. Deep purple crystalline product (260 mg, 61 percent) is recovered. This product is recrystallized from toluene-pentane, and identified as Ta(C$_5$Me$_5$)Cl$_2$(cyclooctene) from the 1H nuclear magnetic resonance spectrum. 1H nuclear magnetic resonance ($\tau$, C$_6$D$_6$) 6.90–9.20 with a broad singlet at 7.33 (m, cyclooctene) and 8.39 (s, C$_5$Me$_5$).

B. Dimerization of 1-Octene

The general procedure of Example 1 is followed. Ta(C$_5$Me$_5$)Cl$_2$(cyclooctene) (177 mg, 0.356 mmole) is dissolved in 2.66 ml of toluene in a 30-ml screw cap vial. Decane (150 $\mu$l, 109.5 mg, 0.77 mmole) is added to the solution for use as an internal gas phase chromatography standard. 1-Octene (1.57 g, 14 mmoles) is added to the solution. The reaction mixture is brought to 50° C. in an oil bath. The reaction is analyzed by the method described in Example 1 and found to contain tail-to-tail dimer 2-hexyl-3-methyl-1-nonene in a selectivity of 84 mole percent. The catalyst activity is found to be 0.046 mol. M$^{-1}$ hr.$^{-1}$ at 50° C.

When Example 2(a) is compared with Comparative Experiment 1, it is seen that the trimethylsilyl-substituted catalyst TaCp$^{s,2}$Cl$_2$(cyclooctene) is about 1.7 times more active at 50° C. than Ta(C$_5$Me$_5$)Cl$_2$(cyclooctene), while maintaining a comparable selectivity.

EXAMPLES 3(a)-(d)

Dimerization of Propylene

Example 3(a) is carried out as follows: All liquid reagents are deoxygenated in three freeze-pump-thaw cycles, then dried over molecular sieves. TaCp$^{s,2}$Cl$_2$(cyclooctene) (210 mg, 0.399 mmole) is dissolved in 40 ml of toluene. Decane (1.8 ml, 1.31 g, 9.2 mmoles) is added to the solution for use as an internal gas phase chromatography standard. The reactor is charged at room temperature with propylene (Matheson, 99.0 percent grade) to a pressure of 150 psig. The temperature is raised to the desired temperature by means of an oil bath. Aliquots are periodically removed from the reactor for analysis by capillary gas phase chromatography, as described in Example 1 (except that the temperature program is 40° C. for 4 minutes rising to 150° C. at 32° C./minute).

Examples 3(b), (c), and (d) are conducted in a manner analogous to that described for Example 3(a). The results of Examples 3(a), (b), (c), and (d) are presented in Table II.

TABLE II

| Ex. 3 | Catalyst/Solvent (mg/ml) | T (°C.) | Selectivity* (mole %) | | |
|---|---|---|---|---|---|
| | | | tt | ht | others |
| (a) | 210/40 | 53 | 95 | | 1.8 |
| (b) | 100/30 | 73 | 94 | 2.6 | 3.3 |
| (c) | 228/30 | 80 | 94 | 2.8 | 3.9 |
| (d) | 210/40 | 98 | 91 | 3.5 | 6.1 |

*tt is the tail-to-tail dimer 2,3-dimethyl-1-butene
ht is the head-to-tail dimer 2-methyl-1-pentene others, include internal olefinic dimers The catalyst activity is found to be the following: (a) 0.8, (b) 2.0, (c) 4.88 and (d) 12.3 mol. M$^{-1}$ hr.$^{-1}$. The tail-to-tail dimer is obtained in a selectivity of greater than 90 percent under mild process conditions.

COMPARATIVE EXPERIMENT 2

The general procedure of Example 2 is followed. Ta(C$_5$Me$_5$)Cl$_2$(cyclooctene) (200 mg, 0.402 mmole), wherein C$_5$Me$_5$ is pentamethylcyclopentadienyl, prepared as in Comparative Experiment 1A, is dissolved in 30 ml of toluene. Decane (1.8 ml, 1.3 g, 9.2 mmoles) is added to the solution for use as an internal gas phase chromatography standard. The reactor is charged at room temperature with propylene to a pressure of 140 psig. The temperature of the reactor is brought up to between 80° C. and 90° C. with stirring. Samples are removed periodically for analysis, as in Example 2, and are found to contain 2,3-dimethyl-1-butene in a selectivity of 96.1 mole percent. The activity of the catalyst is measured at 2.7 mol. M$^{-1}$ hr.$^{-1}$ at 85° C.

When Example 3(c) is compared with Comparative Experiment 2, it is seen that the trimethylsilyl-substituted catalyst TaCp$^{s,2}$Cl$_2$(cyclooctene) is about two times more active at 80° C.–85° C. than Ta(C$_5$Me$_5$)Cl$_2$-(cyclooctene), while maintaining comparable selectivity.

What is claimed is:

1. The catalyst represented by the formula:

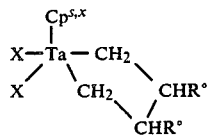

wherein X is halide or alkoxide, R$^o$ is hydrogen or a C$_{1-18}$ alkyl, and Cp$^{s,x}$ is a cyclopentadienyl group containing at least one tri-substituted silyl moiety; said cyclopentadienyl group being represented by the formula C$_5$H$_{5-x}$(SiR$^6_3$)$_x$, wherein each R$^6$ is the same or different and is hydrogen, alkyl, cycloalkyl, aryl, aralkyl or alkoxy, and X is an integer from 1 to 5.

2. The catalyst of claim 1 wherein X is chloride.
3. The catalyst of claim 1 wherein R$^o$ is hydrogen.
4. The catalyst of claim 1 wherein R$^o$ is ethyl.
5. The catalyst of claim 1 wherein Cp$^{s,x}$ is 1,3-[C$_5$H$_3$(SiMe$_3$)$_2$] wherein Me is methyl.
6. The catalyst represented by the formula:

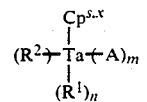

wherein R$^1$ is benzyl or neopentyl; n is 0 or 1; R$^2$ is neopentylidene or benzylidene; A is halide or a moiety of the formula YR$^3$R$^4$R$^5$ wherein Y is a Group Va element and R$^3$, R$^4$, and R$^5$ are the same or different and are C$_{1-4}$ alkyl, aralkyl or aryl, m is 1 or 2, and Cp$^{s,x}$ is a cyclopentadienyl group containing at least one tri-substituted silyl moiety; said cyclopentadienyl group being represented by the formula C$_5$H$_{5-x}$(SiR$^6_3$)$_x$, wherein each R$^6$ is the same or different and is hydrogen, alkyl, cycloalkyl, aryl, aralkyl or alkoxy, and x is an integer from 1 to 5.

7. The catalyst of claim 6 wherein A is a halide.
8. The catalyst of claim 6 wherein A is a moiety of the formula YR$^3$R$^4$R$^5$.
9. The catalyst of claim 8 wherein Y is N.
10. The catalyst of claim 8 wherein Y is P.
11. The catalyst of claim 6 wherein Cp$^{s,x}$ is 1,3-[C$_5$H$_3$(SiMe$_3$)$_2$] wherein Me is methyl.
12. The catalyst of claim 6 wherein R$^1$ is neopentyl.
13. The catalyst of claim 6 wherein R$^2$ is neopentylidene.

* * * * *